United States Patent [19]

Khromov et al.

[11] 3,935,303

[45] Jan. 27, 1976

[54] BASE FOR OPHTHALMOLOGICAL MEDICINAL PREPARATIONS AND ON OPHTHALMOLOGICAL MEDICINAL FILM

[76] Inventors: Gennady Lvovich Khromov, 2 Frunzenskaya ulitsa, 10, kv. 100; Anatoly Borisovich Davydov, ulitsa Krasny Kazanets, 19, korpus 1, kv. 283; Jury Fedorovich Maichuk, ulitsa Usievicha, 11, kv. 4, all of Moscow; Inna Fedorovna Tischina, Schelkovsky raion, poselok Biofabriki, 25, kv, 22, Moskovskaya oblast, all of U.S.S.R.

[22] Filed: Nov. 1, 1972

[21] Appl. No.: 302,820

[52] U.S. Cl. .................... 424/14; 424/16; 424/19; 424/22; 424/78; 128/260
[51] Int. Cl.² ..................................... A61K 27/12
[58] Field of Search .......... 128/260; 424/78, 80, 81, 424/14, 16, 19, 22

[56] References Cited
UNITED STATES PATENTS

| | | | |
|---|---|---|---|
| 3,025,219 | 3/1962 | Maeder............................ | 424/81 X |
| 3,576,760 | 4/1971 | Gould et al. ...................... | 252/403 |
| 3,577,516 | 5/1971 | Gould et al. ...................... | 424/81 |
| 3,577,518 | 5/1971 | Shepherd et al. .................. | 424/47 |
| 3,641,237 | 2/1972 | Gould et al. ...................... | 424/16 |
| 3,697,643 | 10/1972 | Shepherd et al. .................. | 424/63 |
| 3,775,537 | 11/1973 | Lehman et al. .................... | 424/21 |

*Primary Examiner*—Shep K. Rose
*Attorney, Agent, or Firm*—Haseltine, Lake & Waters

[57] ABSTRACT

A base for ophthalmological medicinal preparations consists of a homopolymer of an amide of acrylic acid having a molecular weight from 30,000 to 1,000,000, and/or a copolymer of an amide of acrylic acid with unsaturated compounds, the molecular weight of the copolymer being from 20,000 to 500,000, and containing from 10 to 90 percent acrylamide links.

The ophthalmological medicinal film is an oblong plate, 6–9 mm long, 3 – 5 mm wide and 0.2 – 0.6 mm thick, of the hompolymer and/or copolymer and an active medicinal ingredient, viz., 3-ethyl-4(1-methyl-5-imidazolyl)-tetrahydrofuran-2-one or atropine, or 3-methoxy-6-sulfanilamidopyridazine, or β-dimethylamino-ethyl-p-butylaminobenzoate, or neamine, or 5-iodo-2-desoxyuridine.

The ophthalmological medicinal film is used for treatment of glaucoma of various forms, thrombosis of the central vein of the retina, atrophy of the optic nerve, for dilating the pupil and paralysis of accommodation in treatment of keratitis, iritis, iridocyclitis, ulcers of the cornea, trachoma, herpetic keratitis, uveitis and adenoviral infections, in extraction of foreign objects from the eye, and in various interventions in the organ of vision.

5 Claims, No Drawings

BASE FOR OPHTHALMOLOGICAL MEDICINAL PREPARATIONS AND ON OPHTHALMOLOGICAL MEDICINAL FILM

This invention relates to a new base for ophthalmological medicinal 12) preparations and a new ophthalmological medicinal film. preparations. opthalomology The described biologically soluble polymeric base for ophthalmological medicinal preparations, biologically compatible with eye tissues, is intended for therapeutic treatment of various diseases in ophthalmological practice and for ensuring prolonged action of the medicinal preparations A new ophthalmological medicinal film is used in ophthalmology as a therapeutic remedy.

Polymeric films are known to be used for medical purposes. These are mostly biologically inactive films, used as membranes in medical apparatus (apparatus for extracorporeal blood circulation, such as artificial kidney, artificial heart, etc.) and used also in the pre- and post-operative processing of the wound surfaces. These films are biologically inert with respect to the tissues of the living body, and are liable neither to dissolve nor be assimilated under the action of liquid tissue substrates.

Soluble, assimilable or biologically compatible films are only known to be used in the treatment of skin burns. These are films on the base of natural biopolymers, such as collagen or gelatin.

Also known is an insoluble polymeric film based on polyvinyl alcohol which is a vehicle for administration of a medicinal preparation into the conjunctival cavity, and which is removed from the cavity after the active ingredient has been absorbed. The disadvantage of said insoluble polymeric film resides in that it swells in the lacrimae which causes irritation of the eye mucosa.

The literature does not contain a description of biologically soluble polymeric films used in ophthalmological practice.

According to the invention, the base for ophthalmological medicinal preparations consists of a homopolymer of acrylamide having a molecular weight of 30,000 - 1,000,000 and/or a copolymer of acrylamide with unsaturated compounds having a molecular weight in the amount of from 20,000 to 500,000 and containing acrylamide links from 10 to 90 per cent.

The said base should preferably contain N-vinyl pyrrolidone, N-vinyl caprolactam, the ethyl, acrylate acid, butylacrylate or vinylacetate as unsaturated compounds.

The base can be a 0.1 - 20 per cent aqueous solution of a homopolymer of acrylamide and/or a copolymer of acrylamide with unsaturated compounds having a molecular weight from 20,000 to 500,000 and containing acrylamide links in the amount of 10 to 90 per cent.

The said base can also be a 0.1–30 percent aqueousalcholic solution of a homopolymer of acrylamide having a molecular weight from 30,000 to 1,000,000 and/ or a copolymer of acrylamide with unsaturated compounds having a molecular weight of the copolymer from 20,000 to 500,000 and containing acrylamide links in the amount of from 10 to 90 per cent. A 30 – 70 per cent aqueous-ethanol solution should preferably be used as the aqueous-alcoholic solution. The new base can be used in the manufacture of a new medicinal preparation, namely medicinal ophthalmological film containing various active ingredients, such as miotics, mydriatics, sulfanilamides, antibiotics, anesthetics, antiviral preparations, and can also be used for preparing medicinal opthalmological solutions.

The medicinal ophthalmological film, according to the invention is an oblong plate, 6 – 9 mm long 3 - 5 mm wide, 0.2 – 0.6 mm thick, consisting of a homopolymer of acrylamide having a molecular weight from 30,000 to one-million and/or a copolymer of acrylamide with unsaturated compounds, the molecular weight of the copolymer being from 20,000 to 500,000 and containing acrylamide links in the amount of from 10 to 90 per cent, and the active ingreient, via 3-ethyl-4(1-methyl-5-imidazolyl)-tetrahydrofuran -2-one, atropine, 3-methoxy-6-sulfanilamidopyridazine, $\beta$-dimethylaminoethyl-p-butylaminobenzoate, neamine or 5-iodo-2-desoxyuridine. The said ophthalmological medicinal film should preferably contain from 2 to 15 mg of 3-ethyl-4(1-methyl-5-imidazolyl)-tetrahydrofuran-2-one, or not more than 3 mg of atropine, or not more than 15 mg of 3-methoxy-5-sulfanilamidopyridazine, or not more than 10 mg of $\beta$-dimethylaminoethyl-p-butylaminobenzoate, or not more than 5000 units of neamine, or from 0.5 to 2 mg of 5-iodo-2-desoxyuridine. Depending on the particular active ingredient contained in the ophthalmological film, it can be used in the treament of bacterial viral infections and some pathological changes of the eye.

In some cases, the use of the ophthalmological medicinal films, owing to their prolonged action, rules out the subconjunctival injections of medicinal preparations. Ophthalmological medicinal films are used in glaucoma of various forms, thrombosis of the central vein of the retina, atrophy of the optic nerve, for dilating the pupil and in paralysis of accommodation, in the treatment of keratitis, iritis, iridocyclitis, ulcers of the cornea, trachoma, herpetic keratitis, uveitis, and adenoviral infections, in extraction of foreign objects, and in various operative interventions. After the ophthalmological medicinal film has been introduced into the conjunctival cavity, it is quickly dissolved and assimilated, the rate of these processes depending on the structure and the composition of the polymer base.

The medical experimental, toxicological and pharmaceutical tests of the ophthalmological medicinal films containing the above named active ingredients have revealed advantages of this film over medicinal preparations in the other medicinal forms. It is impossible to ensure accurate dosages of preparations used in various known ophthalmological medicinal forms, such as solutions or ointments. For example if a solution is administered in the form of drops, the variation of a 0.05 - - 0.1 ml dose is as large as 30 – 40 per cent, which is due to the loss of one million preparation with the tears (the lacrimation being intensified by the administration of the preparation), or merely due to the overflow in the eye-lid. ingredient, viz. -imidazolyl)-tetrahydro-furan- When a medicinal preparation is administered in the form of a film, the intensified lacrimation in the first moment after administration only facilitates moistening of the film and promotes its dissolution. This retains the preparation in the eye and the variation of the dose (that is, the dosage error) is practically nullified, which is very important, especially when strong medicinal preparations are used. Moreover, the use of biologically soluble polymeric films in treating eye diseases decreases the number of sessions to one per day (in exacebations) or one per two days, instead of 5 to 8 applications of the medicinal preparation in the form of drops or ointments. Owing to the prolonged action of the medicinal films, the methodology of the therapy is markedly simplified, and the patients and the medical personnel are freed from frequent sessions. The consumption of the medicinal preparations is decreased, the danger of side effects is minimized, and the terms of treatment are shortened.

The medicinal ophthalmological films have been tested clinically. These were films on the above mentioned basis, containing active ingredients such as 3-ethyl-4-(1-methyl-5-imidazolyl)-tetrahydrofuran-2-one or atropine, or 3-methoxy-6-sulfanilamidopyridazine, or $\beta$-dimethylaminoethyl-p-butylaminobenzoate, or neamine, or 5-iodo-2-desoxyuridine. The preparations were tested on 250 patients with various eye diseases (conjunctivites, keratites, iridocylcites, corneal errosion, herpetic keratites, keratouveites, etc.). Films were applied once a day in the anterior part of the conjunctival cavity. The use of films with 3-methoxy-6-sulfanilamidopyridazine in patients with corneal errosion (after extraction of extraneous objects or chemical burns of the first degree) the healing term was 2–3 days. In patients with pneumococcous conjunctivitis the treatment was continued for 6 to 9 days, and no pheumococci were detected microbiologically in the repeated smears from the conjunctiva on the second day of the treatment. The ophthalmological film containing atropine was used in patients with inflammatory diseases of the iris with posterior synechia. A positive effect was noted in all cases. The effect consisted in the following: the injections of the eye ball decreased, the pupil was somewhat dilated, and fine synechia were ruptured. The number of applications of mydriatics decreased. The sensation of dryness in the mouth and tachycardia, which are characteristic of frequent applications of aqueous solutions of atropine, were absent The ophthalmological medicinal film containing 5-iodo-2-desoxyuridine was used in patients with herpetic keratitis and keratouveitis. The use of the film accelerated the healing process and relieved patients of multiple applications of the suspension of the preparation which is practically insoluble in water.

No side effects were noted during clinical trials of the ophthalmological medicinal films.

There are no contraindications to the use of the ophthalmological medicinal films. The investigations on the use of the ophthalmological medicinal films have shown that they possess sufficient mechanical strength, and their weight varies only insignificantly (not over +10 per cent). The variation in the medicinal substance content of the film is insignificant and falls within the limits of the analytical error. The film was also tested after 12 -and 24-month storage. The results show that it retains its stability in this respect. The ophthalmological medicinal film should be stored at a temperature from minus 40°to plus 40°C.

For the purpose of identification of films containing various active ingredients and thus to exclude mistakes in the use of the ophthalmological medicinal films, they are specifically colored (red and green) by adding methyl red and brilliant green into the films containing atropine or 3-ethyl-4-(1-methyl-5-imidazolylmethyl)-tetrahydrofurane-2-one, respectively.

The ophthalmological medicinal film can be prepared by the following procedure.

A 0.1 – 20 per cent solution of a homopolymer of acrylamide having a molecular weight of 30,000 – 1,000,000 and/or a copolymer of acrylamide acid with unsaturated compounds, the molecular weight of the copolymer being from 20,000 to 500,000, and containing acrylamide links in the amount of from 10 to 90 per cent in distilled water is prepared and the precalculated quantity of the active principle is added to it. The solution is homogenized and poured onto a level surface in a 4-8 mm thick layer. (The surface is polished and pretreated with an antiadhesive agent). The layer is dried at a temperature from 20°to 25°C until the residual moisture is 5– 7 per cent. By using a special punch, the film is cut into required shapes and sizes. The punched films are sterilized and packed.

Another method can also be used. A finely dispersed homopolymer of acrylamide having a molecular weight of 30,000 to 1,000,000 and/or a copolymer of acrylamide with an unsaturated compound having a molecular weight from 20,000 to 500,000 and containing acrylamide links from 10 to 90 per cent at a precalculated dose of the active ingredient are placed into a reaction vessel provided with a high-speed stirrer (5,000–20,000 rpm). An aqueous-alcoholic solvent, for example, ethanol-water is added and the components are mixed for 30 to 60 minutes. The thus-prepared finely dispersed suspension or a colloidal solution is dried to prepare the ophthalmological medicinal film similar to that prepared in the previous example.

Still another method for preparing the ophthalmological medicinal film is effected as follows.

A mixture consisting of the above-named polymer and the required quantity of the active ingredient is placed into a reaction vessel equipped with a high-speed stirrer (500 – 20,000 rpm) and mixed for 10 to 30 minutes. The thus-prepared finely dispersed composition is kept for 30 to 180 minutes at room temperature and humidity of 98 per cent. The moist mixture (relative humidity from 10 to 50 per cent) is batched and stamped under a pressure from 200 to 800 kg/sq.cm to obtain films of the required shape and size. The films are sterilized and packed.

This method of preparing the ophthalmological medicinal film should be used for preparing polymeric films with active ingredients which are substances insoluble in water and organic solvents or decomposing on lengthy contact with water, and also for preparing ophthalmological medicinal films from polymers sparingly or slowly soluble in aqueous media.

For a better understanding of the invention it will be illustrated by examples of practical embodiments of the method for preparing the ophthalmological medicinal film.

EXAMPLE 1

The base for the ophthalmological medicinal film has the following composition (in parts by weight):
homopolymer of acrylamide, mol. weight 500,000 1.0
distilled water 99.0
990 g of distilled water are placed into a reaction vessel and 10 g of a homopolymer of acrylamide having a molecular weight of 500,000 are added with constant stirring. The components are mixed to ensure complete dissolution of the homopolymer, and the mixture is then filled into vials, sealed and sterilized.

EXAMPLE 2

The base for the opthalmological medicinal film has the following composition (in parts by weight):

homopolymer of acrylamide, mol. weight 350,000 4.0
copolymer prepared on the basis of acrylamide, N-vinylpyrrolidone and vinyl acetate taken in the ratio (0.2 : 0.3 : 0.5) and having a mol. weight of 70,000 6.0
ethyl alcohol 45
distilled water 45

Into the reaction vessel are charged 45 g of ethyl alcohol, 45 g of distilled water, and then 6 g of the said copolymer and 4 g of the homopolymer of acrylamide are added successively with stirring. The components are stirred until the said polymers are completely dissolved, and the solution is then filled into vials. The thus-obtained base is used for preparing the ophthalmological medicinal film.

EXAMPLE 3

The ophthalmological medicinal film is an oblong red plate, 9 × 4.5 × 0.35 mm and consisting of a copolymer of acrylamide, N-vinylpyrrolidone and ethyl acrylate containing 60 per cent of acrylamide links in a polymeric macromolecule having a molecular weight of 700,000, 2.4 mg of the active ingredient (atropine) and 2.5 mg of the stain (methyl red). The film is prepared as follows.

Into a reaction vessel are charged 90 g of distilled water and then 10 g of the said copolymer and 1.2 g of atropine and 2.5 mg of the stain (methyl red) are dissolved successively with stirring.

The thus-prepared solution is poured onto a polished level surface in a layer 5 mm thick and dried at a temperature from 20° to 40°C for 16 – 20 hours. The dry film has a thickness of 0.35 mm. Films of the required size and shape are punched by a special stamp.

EXAMPLE 4

The ophthalmological medicinal film is an oblong plate 7 mm long, 4 mm wide and 0.4 mm thick, containing a copolymer of acrylamide, N-vinylcaprolactam and ethyl acrylate containing 53 per cent of acrylamide links in a macromolecule having a mol. weight of 420,000 and 4 mg of the active ingredient β-dimethylaminoethyl-p-butylaminobenzoate.

The ophthalmological medicinal film of the above composition is prepared as follows. Into a reaction vessel are loaded 90 g of distilled water, and then 10 g of the said copolymer and 2 g of the active ingredient, β-dimethylaminoethyl-p-butylaminobenzoate are added successively with stirring. The film is prepared from the homogeneous solution by the method described in Example 3.

EXAMPLE 5

The ophthalmological medicinal film is an oblong plate, white in color, 8.5 mm long, 4 mm wide, 0.35 mm thick, consisting of the copolymer N-vinylpyrroliodone, acrylamide and butylacrylate taken in the ratio of 0.3 : 0.4 : 0.3 and containing 42 per cent of acrylamide links in the polymer macromolecule having a mol. weight of 270,000 and 1 mg of the active ingredient, 5-iodo-2-desoxyuridine.

The said ophthalmological film is prepared as follows. To 10 g of the said copolymer are added 500 mg of 6-iodo-2-desoxyuridine and moistened (to 15 per cent) by placing it in a thin layer into a chamber having a humidity of 98 per cent and keeping it there for three hours. The moist polymer containing the active ingredient is placed in an atomizer where it is disintegrated and mixed for ten minutes. Then, 20 mg of the polymer mixture are placed into a mold and the ophthalmological medicinal film of the required size and shape is prepared under a pressure of 400 – 500 kg/sq. cm.

EXAMPLE 6

The ophthalmological medicinal film is an oblong yellow plate, 9 mm long, 4.5 mm wide and 0.35 mm thick consisting of a copolymer of acrylamide, N-vinylpyrrolidone and vinylacetate prepared by copolymerization of the monomers taken in the ratio of 0.3 : 0.5 : 0.2 and containing 33 per cent of acrylamide links in a polymer macromolecule having a molecular weight of 360,000, and 5.2 mg of the active ingredient, 3-methoxy-6-sulfanilamidopyrazine.

The said film is prepared by the following procedure. Into a reaction vessel are charged 80 g of distilled water, and then 10 g of the said copolymer and 10 g of the active ingredient 3-methoxy-6-sulfanilamidopyridazine are added successively with constant stirring until the components are completely dissolved.

The thus-prepared solution is poured onto a polished level surface in a 3-mm thick layer and processed as described in Example 3.

EXAMPLE 7

The ophthalmological medicinal film is an oblong green plate, 9 mm long, 4.5 mm wide, and 0.35 mm thick, consisting of a homopolymer of acrylamide having a mol. weight of 630,000 and a copolymer of acrylamide with N-vinylpyrrolidone and ethyl acrylate, prepared by copolymerization of monomers taken in the ratio of 0.25 : 0.25 : 0.5, having the molecular weight of 120,000, 8 mg of the active ingredient, 3-ethyl-4(1-methyl-5-imidazolyl)-tetrahydrofuran-2-one and 3 mg of the stain, viz., brilliant green.

The said film is prepared by the following procedure. Into a reaction vessel are placed 30 g of ethyl alcohol and 60 g of distilled water, and then 7 g of the said copolymer, 3 g of the homopolymer of acrylamide, 4 g of the active ingredient and 3 mg of the stain, viz., brilliant green are added successively with stirring. The ingredients are mixed to prepare a solution which is then poured onto a polished level surface in a 5-mm thick layer and dried at a temperature of 20° – 40° C for 10 – 16 hours until the residual moisture content is 10 – 15 per cent. The thus-prepared band is separated into films of the required size and shape by using a special punch.

EXAMPLE 8

The ophthalmological medicinal film is an oblong plate, 9 mm long, 4.5 mm wide and 0.35 mm thick, consisting of a copolymer prepared on the basis of N-vinylpyrrolidone, acrylamide, and vinylacetate, taken in the ratio of 0.3 : 0.2 : 0.5 having a molecular weidht of 70,000 and a homopolymer of acrylamide having a molecular weight of 350,000 and 1 mg of the active ingredient, viz., neamine.

The said ophthalmological film is prepared as follows. To 100 g of the base, prepared by a procedure similar to that described in Example 2, are added 100 mg of the active ingredient neamine, the components are mixed to complete dissolution and the ophthalmological medicinal film is molded by the procedure similar to that described in Example 3.

What is claimed is;

1. An ophthalmological medicinal film which is an oblong plate, 6 – 9 mm long, 3 – 5 mm wide, and 0.2 – 0.6 mm thick consisting of a biologically soluble, assimilable copolymer of acrylamide, N-vinylpyrrolidone and butyl acrylate having a molecular weight from 20,000 to 500,000 and containing 10 to 90 per cent acrylamide links and an ophthalmological medicinal agent, selected from the group consisting of 3-ethyl-4(1-methyl-5-imidazolyl)-tetrahydrofuran-2-one, atropine, 3-methoxy-6-sulfanilamidopyridazine, β-dimethylaminoethyl-p-butylaminobenzoate, neamine and 5-iodo-2-desoxyuridine, said film characterized by prolonged medicinal action in the eye.

2. A film according to claim 1, wherein the copolymer contains 42% acrylamide, and the ratio of acrylamide, N-vinylpyrrolidone and butyl acrylate is 0.4 : 0.3 : 0.3.

3. In the treatment of eye disorders by the application to the eye of a film containing an active ophthalmological medicinal agent, the improvement consisting of the step of applying in the anterior part of the conjunctival cavity of the eye a film being dissoluble in lacrimal fluid, having a prolonged medicinal action in the eye, and consisting of biologically soluble, assimilable copolymer of acrylamide, N-vinylpyrrolidone and butyl acrylate having a molecular weight from 20,000 to 500,000 and containing 10 to 90 per cent acrylamide links and an active ophthalmological medicinal agent.

4. The improvement of claim 3, wherein the medicinal agent is selected from the group consisting of 3-ethyl-4(1-methyl-5-imidazolyl)-tetrahydrofuran-2-one, atropine, 3-methoxy-6-sulfanilamidropyridazine, β-dimethylaminoethyl-p-butylaminobenzoate, neamine and 52-desoxyyuridine.

5. The improvement of claim 3, wherein the copolymer contains 42% acrylamide and the ratio of acrylamide, N-vinyl-pyrrolidone and butyl acrylate is 0.4 : 0.3 : 0.3.

* * * * *